United States Patent [19]

Boyle

[11] Patent Number: 4,948,725
[45] Date of Patent: Aug. 14, 1990

[54] TYPE VI BACTERIAL FC RECEPTORS

[75] Inventor: Michael D. P. Boyle, Gainesville, Fla.

[73] Assignee: University of Florida Research Foundation, Inc., Gainesville, Fla.

[21] Appl. No.: 131,071

[22] Filed: Dec. 10, 1987

[51] Int. Cl.$^5$ .................. G01N 33/53; G01N 33/532; C12Q 1/02; C12N 1/00
[52] U.S. Cl. ........................................ 435/7; 435/810; 435/29; 435/243; 435/885; 436/518; 436/544; 436/808
[58] Field of Search ............... 435/885, 7, 29, 34, 435/170, 243, 176, 810; 436/501, 525, 828, 513, 808, 546, 544; 530/413, 320

[56] References Cited

U.S. PATENT DOCUMENTS 4,313,734  2/1982  Leuvering ........................ 436/525
4,617,262 10/1986  Maxim et al. ..................... 436/828

FOREIGN PATENT DOCUMENTS 7900256  5/1979  PCT Int'l Appl. ................. 436/828

OTHER PUBLICATIONS

Yarnall et al., Biochem. Biophys. Res. Commun., vol. 153(3), Mar. 26, 1986, pp. 1105-1111.
Wallner et al., Appl. Microbiol. Biotechnol., vol. 27(2), Oct. 27, 1987, pp. 168-173.
Yarnall et al., J. Gen. Microbiol., vol. 132(7), 1986, pp. 2049-2052.
Goding, Monoclonal Antibodies: Principles and Practice, Second Edition, 1986, pp. 59-103.
Siddle, Alternative Immunoassays, Edited by Collins, 1985, pp. 13-26.
Sevier et al., Clin. Chem., vol. 27(11), 1981, pp. 1797-1806.
Yarnall et al., J. Microbiol. Methods, vol. 3(2), 1984, pp. 83-93.
Von Mering et al., Mol. Immunol., vol. 23(8), Aug. 1986, pp. 811-821.
Reis et al., J. Microbiol. Methods, vol. 4(1), 1985, pp. 45-68.
Nilsson et al., Molecular Immunology, vol. 19(1), 1982, pp. 119-126.
Myhre et al., Infection and Immunity, vol. 27(3), 1980, pp. 808-816.

*Primary Examiner*—Esther M. Kepplinger
*Assistant Examiner*—Florina B. Hoffer
*Attorney, Agent, or Firm*—Saliwanchik & Saliwanchik

[57] ABSTRACT

Novel Fc receptors, denoted type VI, are disclosed as reacting with rat immunoglobulins with a reasonable affinity. These receptors, or the microorganisms which produce them, are useful in immunoassays.

2 Claims, 4 Drawing Sheets

TYPE VI BACTERIAL FC RECEPTORS

Work disclosed herein was supported, in part, by a grant from the National Science Foundation, i.e., NSF, 8500512 DCB.

BACKGROUND OF THE INVENTION

Bacterial Fc receptors have been identified by their ability to bind to a site within the constant region of various classes and subclasses of mammalian IgG (Myhre, E. B. and G. Kronvall. 1981. Immunoglobulin specificities of defined types of streptococcal Ig receptors. In: Basic Concepts of Streptococci and Streptococcal Diseases. [Holm, S. E. and P. Christensen, eds.] pp. 209–210, Reed Book, Ltd., Chertsey, Surrey). The Fc region of the IgG antibody molecule is associated with the biological effector properties of the molecule while the antigenic recognition elements are located in the two identical Fab portions of the antibody. Consequently, the interaction of bacterial Fc receptors with constant region determinants on the heavy chain of IgG does not interfere with the ability of the antibody to recognize its antigen; it is this property that makes these receptors so useful as tracers of antibody-antigen interaction (See Boyle, M. D. P. 1984. Applications of bacterial Fc receptors in immunotechnology. Biotechniques 2:334–340.)

To date, five types of bacterial receptors have been described based on the reactivity of whole bacteria with different classes and subclasses of mammalian immunoglobulins. The most extensively characterized receptor is the type I receptor isolated from *Staphylococcus aureus*, and more commonly designated protein A. The type II receptor is found on a few group A streptococci. The type III receptor is present on many group C streptococci and on some human group G streptococci. The type IV receptor is isolatable from a few bovine group G streptococci, and the type V receptor is found on certain *Streptococcus zooepidemicus* strains.

Mouse monoclonal antibodies have achieved broad applications in immunodiagnostics and in the therapy of disease. The ability to rapidly screen for and isolate mouse monoclonal antibodies has been greatly aided by the use of protein A. Monoclonal antibodies prepared in rats have also been developed and have certain advantages over similar reagents prepared in the mouse system. Rat immunoglobulins, however, react poorly with known bacterial Fc receptors, and, consequently, these reagents are of little value for isolation and characterization of rat monoclonal antibodies. Thus, an Fc receptor capable of identifying rat antibodies could be of tremendous value for screening hybridoma supernatants for specific rat immunoglobulination and for their isolation.

BRIEF SUMMARY OF THE INVENTION

The subject invention concerns a novel bacterial Fc receptor, denoted type VI, which reacts, advantageously, with rat immunoglobulins with a reasonable affinity. More specifically, the subject invention concerns a type VI bacterial Fc receptor having a molecular weight of ca. 43,000 daltons, and being further characterized by binding goat, pig, rabbit, mouse, rat, sheep, cow, and human IgG.

The subject invention also concerns a type VI bacterial Fc receptor having a molecular weight of ca. 90,000 daltons. This Fc receptor is present with the 43,000 dalton Fc receptor in the concentrated culture supernatant harvested following growth of the producing bacteria. The 90,000 and 43,000 dalton Fc receptors are separated from other proteins in the mixture by affinity purification on immobilized goat IgG columns. The isolated 90,000 and 43,000 dalton Fc receptors are then separated by molecular sieving chromatography.

These novel Fc receptors are antigenically distinct from type I, II and III Fc receptors, and display unique functional profiles when compared to type IV and type V receptors.

The novel bacterial Fc receptors of the subject invention are producible in large quantities by the novel microbes *Streptococcus zooepidemicus* strain S212, or *Streptococcus zooepidemicus* strain RSS-212.

Further, the subject invention concerns a method for the expansion of the immunoglobulin binding properties of bacterial strains which demonstrate an Fc receptor producing capability. Exemplified herein is the expansion of the immunoglobulin binding properties of *Streptococcus zooepidemicus* strain S212 by use of a colony blotting technique. The strain resulting from this procedure is named *S. zooepidemicus* RSS-212. This microorganism can be used to isolate and/or detect the presence of immunoglobulins, for example, rat IgG. Alternatively, the novel Fc receptors of the invention can be recovered from the microbe by procedures disclosed herein, and the essentially pure Fc receptors can be used in known immunochemical applications.

The novel type VI Fc receptors show approximately 100-fold greater reactivity with rat immunoglobulins than with protein A-positive *S. aureus*, and 30–40-fold higher reactivity for rat IgG than type III Fc receptor positive streptococcal group G strains. Thus, the novel type VI Fc receptors of the invention, or bacteria exhibiting type VI Fc receptor activity, can be used in immunochemical applications in general since they show affinity for IgG from a broad group of species. The novel Fc receptors are especially useful in quantitation and isolation of rat immunoglobulins.

Autoradiographs were developed following 24 hours exposure to XAR-5 X-ray film.

| | | | |
|---|---|---|---|
| A | *Staphylococcus aureus* | Cowan I | (type I Fc receptor) |
| | | 2 | Docket No. UF/S&S-1 Serial No. 131,071 |
| B | Group A streptococcus | 64/14/HRP | (type II Fc receptor) |
| C | *Streptococcus equisimilus* | 26RP66 | (type III Fc receptor) |
| D | Human group G streptococcus | G1400 | (type III Fc receptor) |
| E | Bovine group G streptococcus | BG8 | (type IV Fc receptor) |
| F | *Streptococcus zooepidemicus* | H1 | (type V Fc receptor) |
| G | *Streptococcus zooepidemicus* | S212 | (provisionally designated type VI) |

Figure 2:
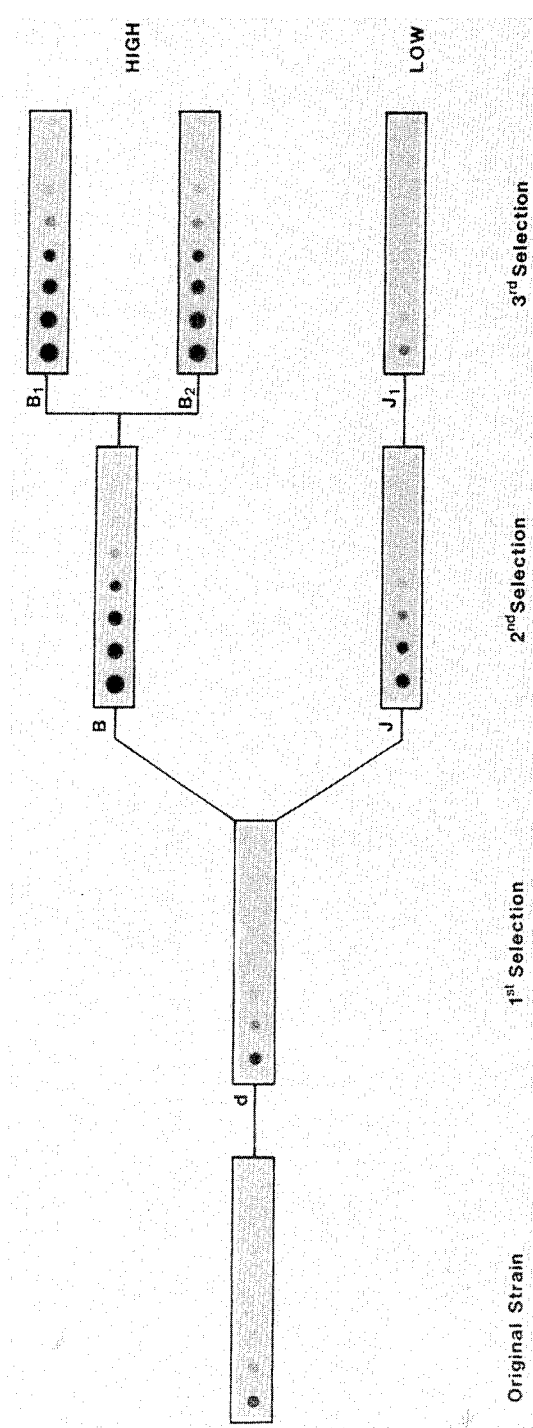

FIG. 2 - Enhancement of rat Fc receptor expression as monitored by dot blot autoradiograph analysis of strains isolated from different selection steps.

The experiments were carried out with 2-fold dilutions of bacteria starting with a $1 \times 10^8$ bacteria/well.

The blots were probed with $^{125}$I-labeled polyclonal rat IgG as described in the Methods.

d represents a high Fc receptor colony selected from the original isolate.

B is a high Fc receptor positive colony selected from d.

B$_1$ and B$_2$ are individual high Fc receptor positive colonies selected from B.

J is a low Fc receptor positive colony selected from d.

J$_1$ is a low Fc receptor positive colony selected from J.

Figure 3:
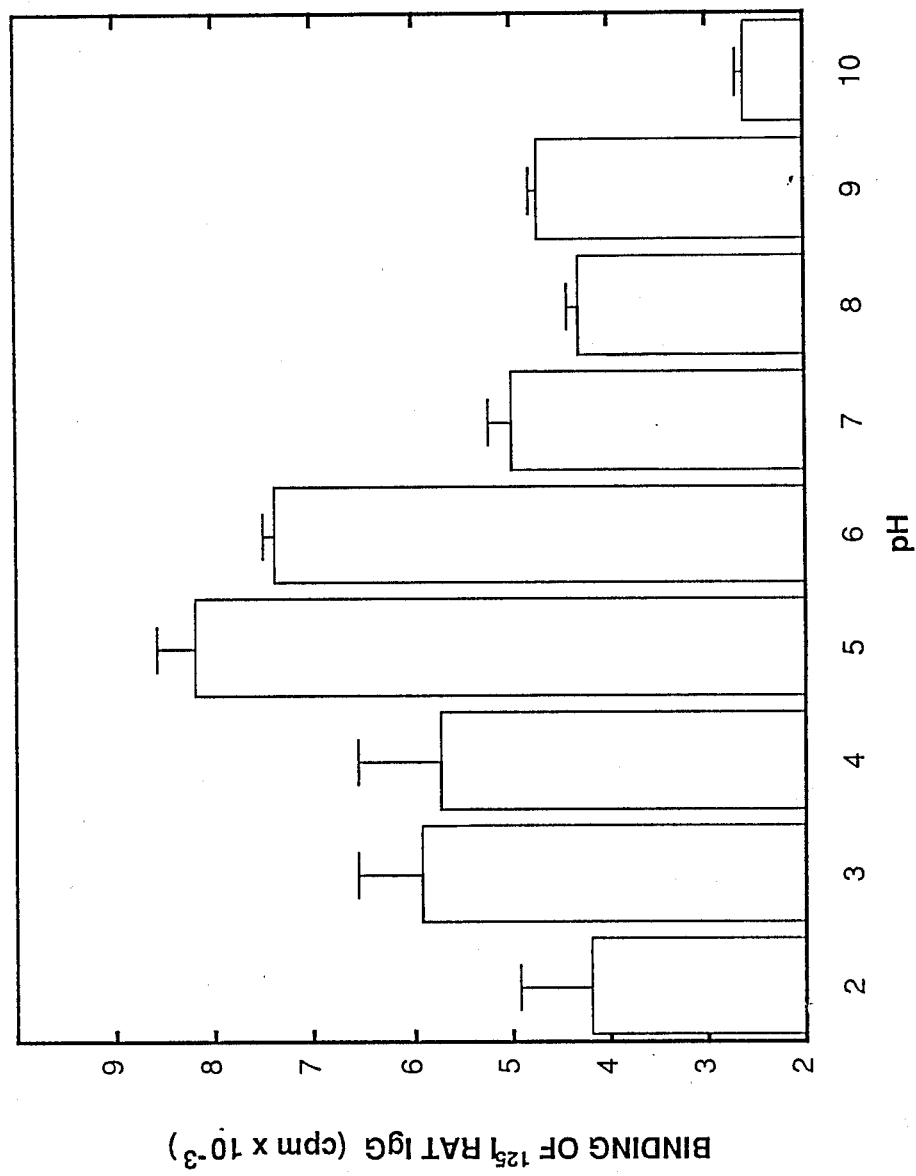

FIG. 3 - Binding of $^{125}$I-labeled polyclonal rat IgG as a function of pH to the selected *Streptococcus zooepidemicus* strain (RSS-212).

Figure 4:
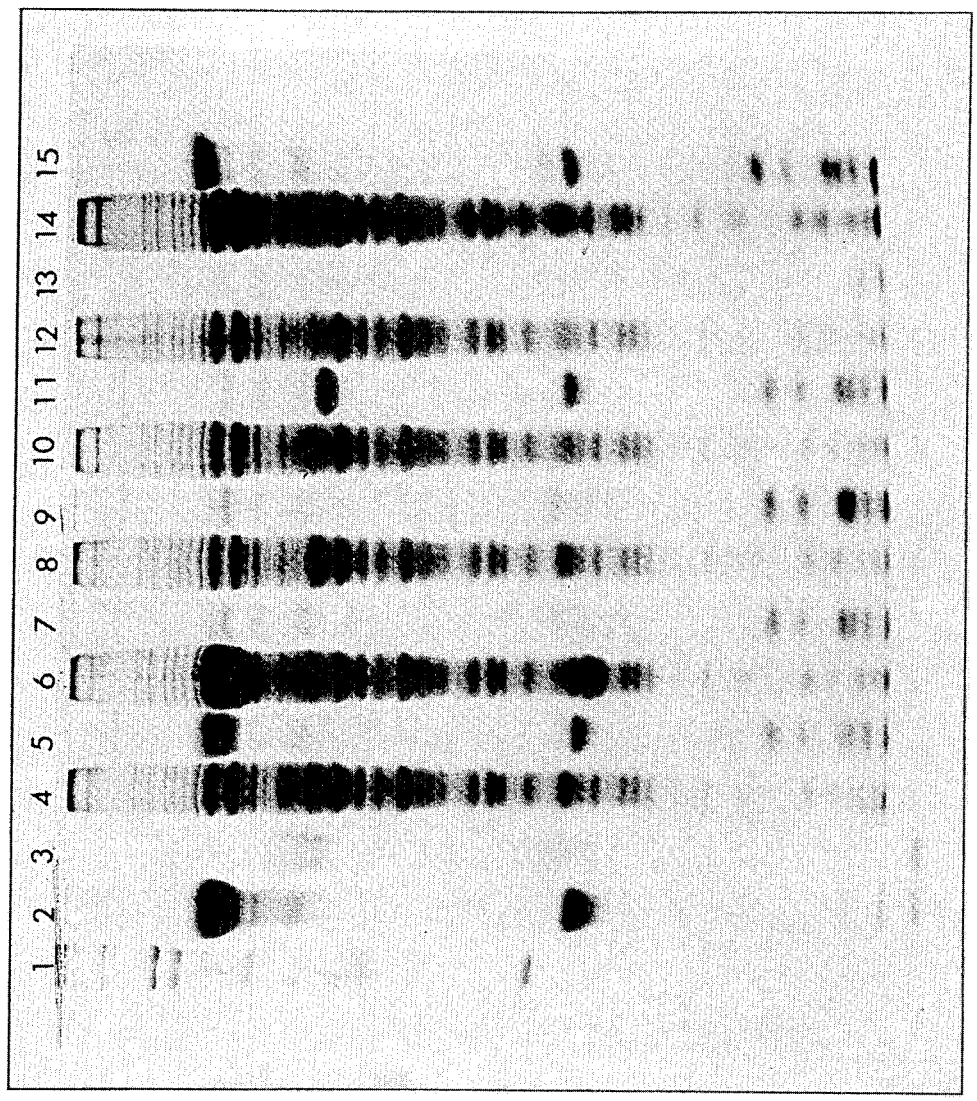

FIG. 4 - Monoclonal antibodies bound to *Staphylococcus aureus* or *Streptococcus zooepidemicus* strain RSS-212.

Lane 1, Σ HMW markers; Lane 2, MOPC 104E murine IgM; Lane 3, murine hybridoma SP39 IgG; Even-numbered lanes 4–14 *Staphylococcus aureus* Cowan I; Odd-numbered Lanes 5–15 *Streptococcus zooepidemicus* strain RSS-1212. Lanes 4 and 5, B23.1 IgM rat monoclonal antibody to a mast cell determinant (Katz et al. supra). Lanes 6 and 7, RA3-3A1 (IgM) rat anti-murine B220 antigen (Coffman et al. supra). Lanes 8 and 9, Bet 1 (IgG$_1$) rat anti-murine IgM (Kung et al supra). Lanes 10 and 11, 14.8 (IgG$_{2b}$) rat anti-murine B220 (Kincade et al. supra). Lanes 12 and 13, control supernatant. Lanes 14 and 15, IgE murine monoclonal anti-TNP antibody (Rudolph et al. supra).

DETAILED DESCRIPTION OF THE INVENTION

Figure 1:
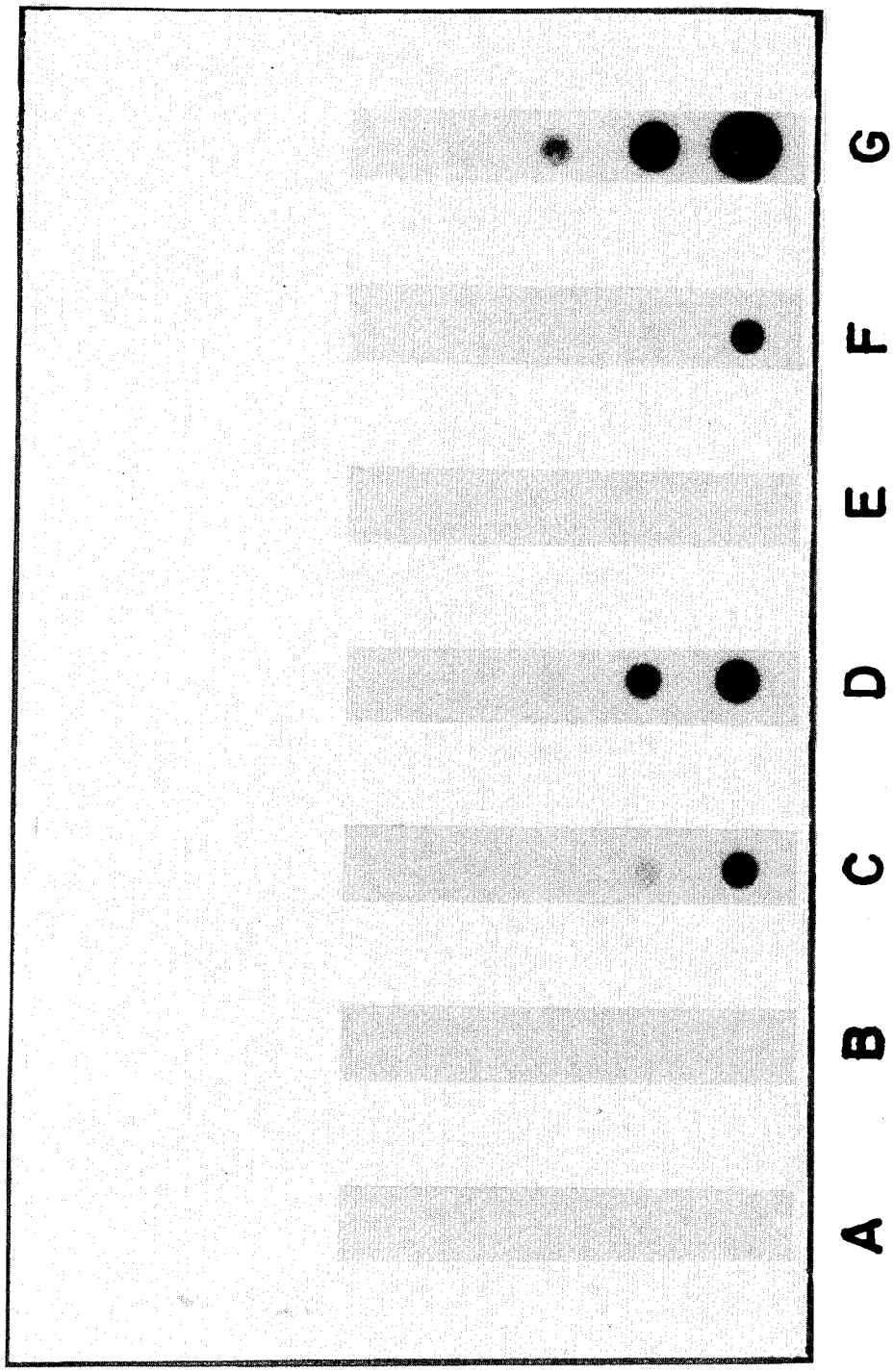
FIG. 1 - Representative autoradiograph demonstrating binding of $^{125}$I-labeled rat Ig to seven Fc receptor-positive strains of bacteria.

The novel type VI bacterial Fc receptors of the subject invention were discovered during an extensive screening program of a variety of bacterial isolates for binding of $^{125}$I-rat IgG. The results presented in FIG. 1 demonstrate the binding of 125I-rat IgG to five-fold dilutions of representative bacterial strains expressing distinct bacterial Fc receptors. Novel *Streptococcus zooepidemicus* strain S212 shows the greatest binding to rat IgG. This reactivity was approximately 60-fold more efficient on a per bacterium basis when compared to the protein A-positive *Staphylococcus aureus* Cowan I strain and approximately 25-fold more efficient than the protein G-positive streptococcus, G1400.

MATERIALS AND METHODS

Bacterial Strains and Growth Conditions

*Staphylococcus aureus* Cowan I served as the representative type I Fc receptor-positive strain. The group A streptococcal strain 64/14/HRP served as a representative type II Fc receptor-positive strain (Reis, K. J., M. Yarnall, E. M. Ayoub, and M. D. P. Boyle. 1984. Effect of mouse passage on Fc receptor expression by group A streptococci. Scand. J. Immunol. 20, 433–439). *Streptococcus equisimilus* 26RP66, a group C strain, and the group G strain G-1400 served as representative type III Fc receptor-positive strains (vonMering, G. and M. D. P. Boyle. 1986. Comparison of type III Fc receptors associated with group C and group G streptococci. Mol. Immunol. 23:811–821). The bovine β hemolytic group G strain BG8 was used as the representative type IV strain (Boyle, M. D. P. and K. J. Reis. 1987. Bacterial Fc receptors. Biotechnology. 5:697–703.) *Streptococcus zooepidemicus* strain H1 and S212 were used as representative type V and VI Fc receptor-positive strains respectively (Boyle et al. supra). All strains were grown as stationary cultures in Todd Hewitt broth (Difco, Detroit, Mich.) for 18–24 hr. at 37° C., harvested by centrifugation and washed in phosphate buffered saline (PBS), pH 7.2.

IgG and IgG Subclasses

Polyclonal rat IgG was purchased from Pel Freeze (Rogers, Ark.). Subclasses were isolated by classical methods using a combination of ion exchange, molecular sieving and affinity purification (Nilsson, R., E. Myhre, F. Kronvall, and H. O. Sjögren. 1982). Fractionation of rat IgG subclasses and screening for IgG Fc-binding to bacteria. Mol. Immunol. 19:119–126; and Nilsson, R., E. Myhre, G. Kronvall, and H. O. Sjögren. 1983. Different protein A immunosorbents may have different bind specificity for rat immunoglobulins. J. Immunol. Meth. 62:241–245). Purity was judged immunochemically using commercially available subclass specific antibodies. These antibodies were obtained from the following sources: Goat anti-rat IgM (μ chain specific) and Rabbit anti rat IgG (H&L chains specific) were obtained from Cappel Laboratories, Malvern, Pa. Sheep anti rat IgG$_1$ (γ chain specific), Goat anti rat IgG$_{2a}$ (γ chain specific), Sheep anti rat IgG$_{2b}$ (γ chain specific), and Goat anti rat IgG$_{2c}$ (γ chain specific) were obtained from Nordic Immunological Laboratory, Capistrano Beach, Calif.

The isolation and specificity of the monoclonal antibodies used were as follows: The rat IgM and a rat IgG$_{2b}$ monoclonal anti-mouse B220 antigen is described in Coffman, R. L. and I. L. Weisman (1981), B220: a B cell specific member of T200 glycoprotein family, Nature 289:681–683; and Kincade, P. W., G. Lee, T. Watanabe, L. Sun and M. P. Scheid (1981), Antigens displayed on murine B lymphocyte precursors, J. Immunol. 127:2262–2268, respectively. The rat monoclonal anti-mouse mast cell antibody is described in Katz, H. R., P. A. LeBlanc and S. Russell (1983), Two classes of mast cells delineated by monoclonal antibodies, Proc. Natl. Acad. Sci. U. S. A. 80:5916–5918. The mouse IgE anti TNP antibody is described in Rudolph, A. K., P. D. Burrows and M. R. Wabl (1981), Thirteen hybridomas secreting hapten-specific immunoglobulin E from mice of the Ig$^a$ or Ig$^b$ heavy chain haplotype, Eur. J. Immunol. 11:527–529. The rat IgG$_1$ anti-mouse IgM is described in Kung, J. T., S. O. Sharrow, D. G. Siekmann, R. Lieberman and W. E. Paul (1981), A mouse IgM allotype determinant (Igh-6.5) recognized by a monoclonal rat antibody, J. Immunol. 127:873–876.

Iodination of IgG

Purified IgG and IgG subclasses were iodinated by a mild lactoperoxidase method using ENZYMO-BEADS® (Bio-Rad, Richmond, Calif.) as described in K. J. Reis, E. M. Ayoub, and M. D. P. Boyle (1983), Detection of receptors for Fc region of IgG on streptococci, J. Immunol. Meth. 59:83–94. The IgG routinely has a specific activity of 0.3 mCi/mg.

Dot-blotting Procedure

This was done using the Bio-Rad bio-dot microfiltration apparatus and a modification of the Bio-Rad procedure as described in Yarnall, M., E. M. Ayoub, and M. D. P. Boyle (1986), Analysis of surface receptor expression on bacteria isolated from patients with endocarditis, J. Gen. Microbiol. 132:2049–2052. A piece of nitrocellulose previously soaked in 20 mM-Tris, 500 mM NaCl, pH 7.5 (TBS), was placed in the apparatus. Five-fold or two-fold serial dilutions of the bacteria were pipetted into the wells. The bacteria were diluted in TBS, starting with approximately $1 \times 10^8$ bacteria. The concentration of organisms was standardized by measuring the $OD_{550}$. After washing the bacteria in each well with TBS containing 0.5% TWEEN ®20 (United States Biochemical Corporation, Cleveland, Ohio), the nitrocellulose was removed and washed four times in 0.15 M-veronal-buffered saline (VBS), pH 7.35, containing 0.15% TWEEN ®20 and 0.50% gelatin. Each wash was done for 15 min. using 250 ml buffer. The nitrocellulose was then probed for 3 hr. in the VBS/TWEEN ®/gelatin buffer containing $2 \times 10^5$ c.p.m. ml$^{-1}$ of the appropriate $^{125}$I-labeled ligand. After probing., the nitrocellulose was washed four times in 0.01 M-EDTA, 1 M-NaCl, 0.25% gelatin and 0.15% TWEEN ®20 (15 min each wash) and allowed to air dry. All washing and probing steps were done at ambient temperature.

Autoradiographs were prepared from the nitrocellulose blots by exposing them to Kodak XAR-5 film with an intensifying screen for varying times at $-70°$ C. before photographic development.

Adsorption of $^{125}$I-Labeled Rat IgG by Bacteria

The detection of Fc-reactive proteins on the surface of bacteria was determined by the ability of bacteria to bind $^{125}$I-labeled IgG (Reis et al., 1983, supra). Standard aliquots of bacteria were incubated with $^{125}$I-labeled rat IgG at the pH stated. The bacteria were pelleted by centrifugation at $1000 \times g$ for 10 min and washed twice with 2 ml of buffer at the appropriate pH. The radioactivity associated with the bacteria was determined in a Beckman (Fullerton, Calif.) autogamma counter. Each buffer contained 0.15 M NaCl, 0.1% gelatin and 0.05% TWEEN ®20. The pH 2 buffer utilized a glycine-HCl buffer. In the pH range of 3 to 8 a Barbital-acetate buffer system was used. The pH 9 and 10 buffers were glycine-NaOH based.

Adsorption of Rat Immunoglobulin Classes and Subclasses by Bacteria Expressing Fc Receptors Aliquots of purified rat immunoglobulins classes and subclasses were adjusted to either pH 5 or pH 7, resulting in a 2-fold dilution. Each sample was adsorbed with 0.1 g (wet weight) of heat-killed RSS-212 strain. Preadsorbed and adsorbed samples were serially diluted 2-fold and tested against antisera specific for rat IgM or IgG subclasses by gel diffusion in 1% agar prepared in 0.01M phosphate, 0.15M NaCl at pH 7.4.

Colony Immunoblotting Assay

The colony blot immunoassay to monitor the expression of Fc receptors on individual bacterial colonies is described in Yarnall, M., K. J. Reis, E. M. Ayoub, and M. D. P. Boyle [1984], An immunoblotting technique for the detection of bound and secreted bacterial Fc receptors, J. Microbiol. Meth. 3:83-93. Essentially an overnight suspension of bacteria was diluted in Todd-Hewitt broth to give 10-100 colonies when 0.1 ml was plated on Todd-Hewitt agar (Todd-Hewitt broth containing 1.5% agar). The plates were incubated at 37° C. for 16 hr. and replica plated onto blood agar plates (BBL Microbiology Systems, Cockeysville, Md.). A circular piece of nitrocellulose previously soaked in 25 mM Tris, 192 mM glycine (pH 8.3) and 20% v/v methanol was placed on top of the colonies followed by a circular piece of Whatman 3 mm paper. The agar was removed from the petri dish and a piece of 3 mm paper was placed on the bottom of the agar. The bacterial colonies were transferred to the nitrocellulose by electrophoresis at 70V for 3 hr. in the above buffer. This procedure resulted in quantitative transfer of the bacterial colonies as judged by comparing photographs of plates before transfer with the stained nitrocellulose membrane after the electroblotting procedure.

After electrophoresis, the nitrocellulose was washed in veronal buffered saline (VBS) containing 0.25% gelatin and 0.25% TWEEN ®20 for one hour with four 250 ml changes. The nitrocellulose was probed for 3 hr. in the washing buffer containing $2 \times 10^5$ cpm/ml $^{125}$I-labeled rat IgG and a two-fold molar excess of unlabeled F(ab')$_2$ fragments. After probing, the nitrocellulose was washed four times in 0.01 M EDTA, 1 M NaCl, 0.25% gelatin, and 0.25% TWEEN ®20 pH 7.5 for 15 min. each and allowed to air dry. The nitrocellulose blots were autoradiographed by exposing to Kodak XAR-5 film with intensifying screen for 3 days at $-70°$ C.

Analysis by Gel Electrophoresis of Monoclonal Antibody Binding to Bacteria

Monoclonal antibody binding to intact heat-killed Staphylococcus aureus or Streptococcus zooepidemicus strain RSS-212 was carried out as follows: Fifty μl of a 10% W/V suspension of heat-killed bacteria were incubated on a rotator overnight in 1-5 ml of hybridoma supernatant at 4° C. After 2 washes in PBS the adsorbed proteins were solubilized by heating in the electrophoresis sample buffer for 30 min. at 65° C. and fractionated on a 12.5% SDS-polyacrylamide gel at 30 mAmp constant current as described in Laemmli, U. K. (1970), Cleavage of structural proteins during the assembly of the head of bacteriophage T4, Nature (London) 227:680-685.

The novel type VI bacterial Fc receptors of the invention are producible by certain strains of Streptococcus zooepidemicus. Specifically exemplified herein are the strains S. zooepidemicus S212 and S. zooepidemicus RSS-212. Subcultures of these strains have been deposited in the American Type Culture Collection (ATCC), 12301 Parklawn Drive, Rockville, Md. 20852.

| Culture | Accession number | Deposit date |
|---|---|---|
| S. zooepidemicus RSS-212 | ATCC 53697 | Dec. 4, 1987 |
| S. zooepidemicus S212 | ATCC 53698 | Dec. 4, 1987 |

The subject cultures have been deposited under conditions that assure access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing a culture. The depositor acknowledges the duty to replace a deposit should the depository be unable to furnish a sample when requested, due to the condition of the deposit. All restrictions on the availability to the public of the subject culture deposits will be irrevocable removed upon the granting of a patent disclosing them.

The gene encoding the novel type VI bacterial Fc receptors can be probed out of the strains disclosed herein using procedures well-known in the molecular biology art. The isolated gene can be inserted into an appropriate vehicle which could then be used to transform another microbe. The transformed microbe could be used to make the novel type VI bacterial Fc receptor.

Thus, it is well within the skill of those in the genetic engineering art to use the nucleotide sequences encoding the novel type VI bacterial Fc receptors of the subject invention to produce these receptors via microbial processes. Fusing the sequences into an expression vector and transforming or transfecting into hosts, either eukaryotic (yeast or mammalian cells) or prokaryotic (bacterial cells), are standard procedures used in producing well-known proteins, e.g., insulin, interferons, human growth hormone, and the like. Similar procedures, or obvious modifications thereof, can be employed to prepare the novel type VI bacterial Fc receptors by microbial means or mammalian tissue-culture technology in accord with the subject invention.

The various methods employed in the preparation of plasmids and transformation of host organisms are well known in the art. These procedures are described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g. *E. coli* cells, prepare plasmid DNA, electrophorese proteins, and sequence DNA.

Following are examples which illustrate procedures, including the best mode, for practicing the invention. These examples should not be construed as limiting. All percentages are by weight and all solvent mixture proportions are by volume unless otherwise noted.

EXAMPLE 1—Isolation and characterization of a type VI Fc receptor

A series of *Streptococcus zooepidemicus* strains were screened for binding to human IgG. The strain S2–12 was found in the preliminary experiments to bind the greatest quantity of labeled human IgG. This strain was further studied for its binding to different labeled IgG species. The results obtained showed that this strain could bind labeled IgG from goat, pig, human, mouse, rabbit, sheep, rat and cow. All of the IgG sources were labeled to approximately equal specific activity and, consequently, the Fc receptors for goat, sheep or pig IgG seemed to be of higher affinity, or present in greater number, than for human or rabbit IgG. Significant reactivity was also observed with rat, mouse, and cow IgG.

Previously, studies have demonstrated that Fc receptor expression on different bacterial colonies can be heterogeneous. Consequently, in the initial experiments, we screened individual colonies for both surface expression and secretion of Fc receptors, using a goat Fc specific probe. Goat IgG was chosen as the probe because of our previous experience with goat immunoglobulins and their reactivity with Fc receptors. Dilutions of the *Streptococcus zooepidemicus* strain S2-12 were grown on blood agar plates to yield between 10–100 colonies. The colonies were replica-plated onto Todd-Hewitt agar plates, incubated overnight at 37° C. and then transferred. The bacteria were transferred to nitrocellulose by electroblotting and then probed with a $^{125}$I-labeled goat Fc specific probe. This probe contained labeled goat IgG and a two-fold molar excess of unlabeled Fab$_2$ fragments. Previous studies have indicated that only IgG binding via the Fc region is detectable using such a probe (Reis et al., 1983, supra). The results indicate that a strain designated *Streptococcus zooepidemicus* S2-12 was extremely heterogenous with respect to Fc receptor expression. A few colonies demonstrated high levels of surface and secreted receptor activity while others demonstrated only surface expression. Some colonies were negative for Fc receptor expression. A colony that demonstrated high levels of surface and secreted Fc receptor activity was isolated and used for further study. This strain, designated S2-12-1, was shown to maintain a high level of surface and secreted Fc receptor expression on subsequent laboratory passage.

In the next series of studies, we attempted to solubilize Fc receptors from the S2-12-1 subcolony. Bacterial pellets were extracted by a number of different methods, including treatment with the enzyme mutanolysin or heat extraction at neutral, acid or alkaline pH and in the presence of 2% SDS. The solubilized material was analyzed for Fc receptor activity by two methods. The first was a competitive binding assay to determine the total quantity of Fc receptor activity and the second was an immunoblotting technique to establish the number of different molecular species of Fc receptors present in each extract. Secreted Fc receptors were also analyzed by Western blot analysis. Results of these assays are presented in the following Table 1.

TABLE 1

Comparison of Extraction Procedures to Solubilize Type VI IgG-Fc Receptors from *Streptococcus zooepidemicus*, S2-12-1

| Extraction Procedure[1] | FcR units/ml of 10% (w/v) Bacteria Extracted[2] | # of Major, Functionally Active FcR Bands[3] |
|---|---|---|
| Boil 10 min at pH 2 | 17.2 ± 1.0 | 4 |
| Boil 10 min at pH 10 | <1.0 | 0 |
| Boil 10 min at pH 7 | 3.5 ± 0.6 | 2 |
| Boil 10 min at 2% SDS | 13.5 ± 1.8 | 5 |
| Mutanolysin 30 units/ml of 10% bacteria | 3.5 ± 0.2 | 3 |

TABLE 1-continued

Comparison of Extraction Procedures to Solubilize Type VI IgG-Fc Receptors from *Streptococcus zooepidemicus*, S2-12-1

| Extraction Procedure[1] | FcR units/ml of 10% (w/v) Bacteria Extracted[2] | # of Major, Functionally Active FcR Bands[3] |
|---|---|---|
| Crude Culture Supernatant | 397 ± 96[4] | 1-2[5] |

[1] Bacteria were recovered after overnight stationary cultures in Todd-Hewitt broth, washed in PBS and suspended to 10% (w/v) in buffers for extraction. Ten ml of 10% (w/v) bacteria were used for each extraction.
[2] One unit of Fc receptor (FcR) activity was defined as the amount that would inhibit the binding of $^{125}$I FcRc (type III FcR) to goat IgG immobilized on immunobeads.
[3] Determined by SDS-PAGE followed by electroblotting to nitrocellulose, probing with $^{125}$I-labeled goat IgG and autoradiography.
[4] Results are expressed as FcR units per liter of overnight culture in Todd-Hewitt broth. Results reflect determinations from three separate cultures.
[5] Two bands are usually present in crude supernatant and one after affinity purification on goat IgG.

These results indicate that the highest yield of Fc receptor was recovered by treatment with hot acid, but the least heterogeneous form was recovered from the culture supernatant. The secreted material contained two major Fc receptor species, one with an $M_r$ of 90,000 and the other with an $M_r$ of 43,000. This material was affinity purified by binding to a column of immobilized goat IgG, and then eluting the bound receptor with 0.1M glycine-HCl pH2. This treatment resulted in the majority of the Fc receptor activity being present in the 43,000 dalton band, which is isolated in the essentially pure form by standard procedures, for example, by ion exchange, molecular sieving chromatography, affinity chromatography or by electroelution from an SDS polyacrylamide gel following electrophoresis or isoelectric focusing.

The affinity purified secreted receptor was further analyzed for its species reactivity by Western blotting techniques and probing with labeled rat, goat, pig, rabbit, mouse, sheep, cow and human IgG. The results demonstrated the same reactive protein bands in the lanes probed with each of the labeled species' IgGs. This pattern of species reactivity was similar to that observed on intact bacteria.

The 43,000 dalton affinity purified essentially pure type VI Fc receptor was capable of binding goat, pig, rabbit, mouse, rat, sheep, cow and human IgG. The novel type VI Fc receptors of the invention can be used, either alone or in combination with other types of Fc receptors, in the quantitation and isolation of various species of immunoglobulins. The reactivity with rat immunoglobulins is particularly useful.

EXAMPLE 2—Expansion of Binding Properties

Expansion of the binding properties of the *Streptococcus zooepidemicus* strain was achieved by use of a colony blotting technique. Initial use of this technique applied to the *Streptococcus zooepidemicus* strain S212 showed a high degree of heterogeneity of binding of $^{125}$I-rat IgG. Individual colonies of the original strain, corresponding to high rat IgG binding (H) and low rat IgG binding (L) on the autoradiograph, were selected from a replica plate (first selection). These representative high and low Fc receptor-positive isolates were expanded using the colony blotting technique. The selected strains showed a lower degree of heterogeneity of Fc receptor expression. Three cycles of colony selection were performed using the high Fc receptor expressing strain and selecting for the highest levels of Fc receptor expression each time. Dot blots of the original. *S. zooepidemicus* S212 strain and isolates derived from individual colonies selected for either high or low binding of $^{125}$I-rat IgG are shown in FIG. 2. This process resulted in a 10-20-fold increase in binding of $^{125}$I-rat IgG compared to the original strain.

To determine if a similar enhancement occurred in the reactivity of the selected strain with other species of IgG a similar experiment was carried out in which the bacterial colonies were assayed for reactivity with rabbit, goat, and human IgG. Similar enhanced Fc receptor expression was observed when the selected strains were probed with any of these species of IgG, suggesting that the same receptor was probably involved in binding to all IgG species. This high expressing Fc receptor-positive strain is designated RSS212.

The above procedure, or obvious modifications thereof, can be used to expand the immunoglobulin binding properties of any bacterial strain which demonstrates an Fc receptor binding capability.

EXAMPLE 3—Effect of pH on the Binding of $^{125}$I-rat IgG to the High Fc Receptor Strain The practical application of the rat Fc receptors selected strain (RSS-212) for use as an immobilized reagent in place of a second antibody reagent was tested in a number of experiments. In the initial studies, the effect of pH on the binding of $^{125}$I-rat IgG to the RSS-212 strain was measured. Radioiodinated polyclonal rat IgG was incubated with heat-killed RSS-212 ($1 \times 10^{10}$) bacteria at various pH's. Following incubation for 1 hour at 37° C., unbound $^{125}$I-rat IgG was removed by washing and centrifugation in buffers of the same pH. The results showed that the most efficient binding of $^{125}$I-rat IgG occurred at pH 5.

EXAMPLE 4—Binding of Rat Immunoglobulin Classes and Subclasses

In the next series of experiments the ability of different rat IgG classes and subclasses to bind to the selected bacteria was tested as described in the Methods. The results presented in the following Table 2 indicate that the RSS-212 strain bound polyclonal rat IgM, IgG$_1$ and IgG$_{2b}$ with a good affinity while showing minimal reactivity with IgG$_{2a}$. These results show that the RSS-212 strain is useful for certain immunochemical applications involving the polyclonal or monoclonal antibodies of the IgM, IgG$_1$ or IgG$_{2b}$ classes or subclasses.

TABLE 2

Adsorption of Polyclonal Rat Immunoglobulin by RSS-212 Strain at pH5 and pH7

| Rat Immunoglobulin Class/Subclass | Pre-Adsorbed | | Post-Adsorbed | |
|---|---|---|---|---|
| | pH5 | pH7 | pH5 | pH7 |
| IgM | +++ | +++ | 0 | ++ |
| G1 | +++ | +++ | + | +++ |
| G2a | ++++ | ++++ | +++ | ++++ |
| G2b | ++++ | +++ | ++ | +++ |

Rat IgM and IgG subclasses were purified from serum as described in the Methods. Aliquots of each immunoglobulin fraction were adjusted to pH5 or pH7 resulting in a 1:2 dilution of each sample. Each sample was adsorbed with 0.1 g wet weight of the RSS-212 strain. Controls and adsorbed samples were serially diluted 2-fold and tested against antisera specific for rat IgM or IgG subclasses by gel diffusion.
++++ represents precipitation against specific antisera by all dilutions up to and including 1:16 dilution of fraction.
+++ represents precipitation against specific antisera by all dilutions up to and including 1:8 dilution of fraction.
++ represents precipitation against specific antisera by all dilutions up to and including 1:4 dilution of fraction.
+ represents precipitation against specific antisera at 1:2 dilution of fraction.
0 no precipitation at 1:2 dilution of fraction.

EXAMPLE 5—Binding to Rat Monoclonal Antibodies

Previous studies with the protein A-positive *Staphylococcus aureus* Cowan I strain and mouse monoclonal antibodies have indicated that binding of all antibodies of a single subclass is not uniform (Specific monoclonal antibody purification techniques. 1987. Pharmacia Separation News 13:5). For example, certain $IgG_1$ antibodies bind with a high affinity while others fail to bind at all (Pharmacia, supra). In order to explore the reactivity of our rat Fc receptor positive bacteria (RSS212) with a variety of rat monoclonal antibodies we tested the capacity of whole heat-killed bacteria to adsorb monoclonal antibodies from cell culture supernatants. Binding of the antibodies was monitored after washing the bacteria and fractioning the bacterial bound protein by SDS-polyacrylamide gel electrophoresis. The gels were stained with Coomassie blue to identify the protein bands eluted from the bacteria. Heavy and light chains were identified by comparison with purified immunoglobulin standards included on the gel. The binding of one murine and five rat monoclonal antibodies (three rat IgMs, one rat $IgG_{2b}$, one rat $IgG_1$ and a murine IgE) to either the RSS-212 strain or the *Staphylococcus aureus* Cowan I strain were compared. The results presented in FIG. 4 indicate a number of interesting results. Of the three IgM antibodies tested, one bound to RSS-212 (lane 5) and not the *Staphylococcus aureus* Cowan strain (lane 4); one bound to the *Staphylococcus aureus* Cowan strain (lane 6) and not RSS-212 (lane 7) and one antibody bound to neither bacterial strain. The RSS-212 strain showed reactivity with the $IgG_{2b}$ antibody (lane 11) and a murine IgE antibody (lane 15) but not the rat $IgG_1$ antibody (lane 9), despite the strong reactivity of this strain with polyclonal $IgG_1$, Table 2. These findings highlight the fact that not all monoclonal antibodies of a single subclass will behave in a uniform fashion or as predicted from the reactivity of polyclonal antibodies.

The results presented in FIG. 4 suggest that the rat Ig binding Fc receptor positive strain selected may find application for use with certain rat monoclonal antibodies and that preliminary experiments like those shown in FIG. 4 will need to be performed to identify suitable bacterial Fc receptors for use with a given monoclonal antibody.

In order for such interactions to be of value, it is important that the reactivity with the bacteria does not inhibit the ability of the $Fab_2$ portion of the antibody molecule to recognize its antigen. To examine this possibility we have tested the ability of certain monoclonal antibodies when immobilized to bacteria to retain their ability to bind antigens. For these studies we have utilized monoclonal antibodies that recognized a specific epitope or differentiation antigen on two murine hematopoietic cell lines. Reactivity of the immobilized antibody was measured using the specific cell labeling technique previously described by Siden, E. J. and M. L. Siegel (1986), A simple method for the simultaneous detection of Fc receptors and differentiation antigens on normal and neoplastic murine hematopoietic cells, J. Immunol. Meth. 87:251-255. The reactivity observed in this assay demonstrated the same pattern of reactivity that was predicted from the binding properties of the respective bacteria-antibody interactions presented in FIG. 4. These findings suggest that once a reactive bacterial Fc receptor-monoclonal antibody pair has been identified, then the established techniques of immunoprecipitation and cellular labeling developed using protein A reactive antibodies can be expanded to a broader range of experimental systems.

The novel Fc receptors of the subject invention can be employed in a variety of immunotechnology procedures, either with the type VI receptor immobilization or the free form tagged with an appropriate label, such as a radioisotope, an optical label, e.g., a fluorescent tag, an enzyme, an electron dense ligand, and the like. The label may be detected by a gamma counter if the label is a radioactive gamma emitter, or by a fluorimeter, if the label is a fluorescent material. In the case of an enzyme, label detection may be done colorimetrically employing a substrate for the enzyme. All of these procedures are well known in the art. See "Applications of Bacterial Fc Receptors in Immunotechnology," Boyle, Michael D. P., BioTechniques Nov./Dec. 1984, pp. 334-339. This publication and the publications recited therein are incorporated herein by reference thereto.

Immobilization supports or substrates which can be used in the subject invention processes are any inert material generally used in immunochemical assays. Examples of such materials are beads formed of glass, polystyrene, polypropylene, dextran or other material. Other suitable solid phases include tubes or plates formed from or coated with these materials. Commercially available supports are agarose beads, IMMUNOBEADS® and AFI-GEL® 15 activated beads. These are all trademarks of Bio-Rad, Richmond, Calif.

The Fc receptors of the invention may be utilized in any immunoassay method which involves the ability of an antibody to recognize or react with an antigen or antigenic determinant (epitope) and the detection or assay of the resulting antigen-antibody complex.

The present invention embodies any such immunoassay method wherein such detection or assay involves a reaction of the above-described bacterial Fc receptors with mammalian IgG or IgM whereby the Fc receptor binds to the Fc region thereof.

Virtually all such immunoassays involve one or more of the following basic approaches:

(1) Detection of antibodies: The first requirement for developing an immunoassay is the preparation of a specific antibody. In monoclonal antibody techniques this requires a method for screening numerous antibody-secreting clones to identify those that produce antibody with the require antigenic specificity. Similar techniques are required to determine the point at which an immunized animal has mounted a strong specific immune response to a given antigen. Detection of either. polyclonal or monoclonal antibodies requires a method of assaying antibody in antigen-antibody complexes. The bacterial, Fc receptors of the present invention can be efficiently used for this, purpose. In these assays, antibody is allowed to form a complex with immobilized antigen and the excess antibody is then washed away. The antibody in the antigen-antibody complex can then be readily detected by first adding radiolabeled Fc receptor and, after washing, determining the amount of radioactive tracer that remains bound. For these assays, immobilized antigen can be obtained by passive adsorption to plastic surfaces, by covalent attachment to appropriate beads or cells, or by the use of appropriate antigens naturally expressed on cell membranes.

Techniques which employ labeled Fc receptors to detect antigen-antibody complexes are more sensitive and exhibit lower background than methods using labeled second antibodies or Clq. The only limitation of this approach is that the antibodies used must be from a species and of a subclass that reacts with the bacterial Fc receptor. The antibody production in most species can be followed using the Fc receptor of the present invention. Enzyme-labeled or fluorescent-labeled Fc receptor can also be used for these assays.

A modification of the above procedure in which immobilized Fc receptor is utilized to detect antigen-antibody complexes makes it possible to screen for specific antibodies. In this procedure the immobilized receptor is incubated with the antibody-containing sample, washed free of unbound antibody and then incubated with labeled antigen. The ability to bind the particular labeled antigen to the immobilized Fc receptor-antibody complex can be used to detect the presence of specific antibodies. This technique is only semiquantitative and requires that a purified homogeneous antigen is available.

(2) Competitive binding assay to quantify antigen: Once selected, specific antibodies can be used to develop rapid competitive-binding radioimmunoassays. The first stage in this type of assay is to immobilize the antigen onto a suitable solid phase support. Provided the antibody is specific, preparations rich in antigen but not completely purified are quite satisfactory. The antigen can be immobilized by passive adsorption onto a suitable plastic surface or by selective chemical coupling to an insoluble particle, e.g., IMMUNOBEADS ® (Bio-Rad). The ability of free soluble antigen to competitively inhibit the binding of antibody to the immobilized antigen can then be used as a method for quantifying the amount of antigen in any sample. In this assay the quantity of antibody bound to the immobilized antigen is measured by the binding of labeled Fc receptor. By comparing the percent inhibition of binding of antibody caused by an aliquot of an unknown sample to that caused by an aliquot of a known antigen preparation, under identical assay conditions, it is possible to measure the absolute concentration of specific antigen in any. sample.

Antibody prepared against synthetic peptides can be used in conjunction with this technique to detect epitopes on larger proteins. It is known that antibodies can be raised against small synthetic peptides and that these antibodies will recognize antigenic determinants in intact full-sized proteins. This approach has been extended to prepare antibody to synthetic peptides encoded by nucleotide sequences within open reading frames for which a gene product has not yet been identified. Using the specific antibody thus generated and the immobilized synthetic peptide antigen, it is then possible to screen extracts for the presence of a specific protein containing that antigenic structure. Once an extract is found to contain a competing activity, the protein which bears the epitope can be isolated using the competitive binding assay to monitor purification. These approaches have broad applications for detecting a variety of gene products, in particular those coded for by oncogenes.

The possibilities of non-specific inhibition and of inhibition by antigenically related but non-identical molecules apply to all immunoassays reqardless of the tracer used.

(3) Detection of specific antigens by Western blotting techniques: The Western blot technique can be used to follow specific epitopes during protein purification. Samples are electrophoresed on SDS or neutral polyacrylamide gels, and proteins are transferred by electroblotting onto a nitrocellulose membrane. The nitrocellulose is reacted with buffer containing a non-reactive protein, e.g., gelatin, to block any unoccupied, non-specific protein binding sites and is then incubated with specific antibody. After a sufficient period of incubation to allow the formation of antigen antibody complexes, unbound antibody is removed by washing the blot, which is then incubated with labeled Fc receptor for about 1 hr. at 37° C., and, finally, washed free of unbound receptor. The quantity and position of the label remaining bound to the antigen-antibody complex is autoradiographically detected by exposure to X-ray film. Alternatively, enzyme-labeled Fc receptor can be used to identify the position of the antigen-antibody complexes on the blot.

(4) Use of immobilized Fc receptors for the isolation of IgG and IgG subclasses: The ability of immobilized bacterial Fc receptors to interact with free IgG has proven extremely valuable for identifying and isolating a variety of mammalian IgG classes and subclasses. Serum is passed through a column of immobilized Fc receptor and the reactive IgG subclasses bind to the column. This bound IgG can be recovered by elution procedures involving either a change in pH, a change in ionic strength or the use of a chaotrophic agent. Different elution using a pH gradient, for example, can resolve the Fc receptor-bound antibodies into differing subclasses with some species. The use of immobilized Fc receptor is of great value for: (i) isolating IgG from the cell-culture supernatants of hybridoma clones, (ii) separating an antigen-antibody complex from free, soluble antigen, and (iii) depleting serum of IgG for use in a variety of diagnostic assays.

These products have proven extremely efficient for isolating or eliminating a variety of subclasses of IgG with high binding affinity for the bacterial receptors. Antibodies that have been purified by affinity chromatography on immobilized Fc receptor columns are very effective for use in immunoassays in which the Fc receptor is used as tracer.

As disclosed previously, the components to be assayed may be coupled or bonded to any assayable ligand such as a radioisotope, fluorescent tag, bio-assayable enzyme, electron dense tag, and the like. Those skilled in the art, having been exposed to the principles of the present invention, will be cognizant of the types of assayable ligands and methods for coupling them to the components of the methods of the present invention without the exercise of undue experimentation o inventive faculties. For convenience and standardization, reagents for the performance of the immunometric assay can be assembled in assay kits. A kit for identifying antibodies, for example, can include:

(a) an immunoadsorbent, e.g., a polystyrene bead coated with the antigen of interest, e.g., growth hormone;

(b) a diluent for the serum or plasma sample from an immunized or infected animal;

(c) a labeled type VI Fc receptor;

(d) positive control, e.g., serum containing antibody against the antigen of interest, e.g., growth hormone; and (e) a negative control, e.g., pooled sera which does not contain antibody against the antigen of interest.

If the label is an enzyme, an additional element of the kit can be the substrate for the enzyme.

Examples of enzymes which can be used as a label are lactoperoxidase, horse-radish peroxidase, alkaline phosphatase, glucose oxidase or $\beta$-glucuronidase.

Examples of radioisotope labels which can be used are $125_I$, $131_I$, $3_H$, $14_C$ or $35_S$.

Examples of electron dense ligand labels which can be used are ferritin, gold or horse-radish peroxidase.

I claim:

1. A kit for use in identifying antibodies comprising:
   (a) an immunoadsorbent comprising the antigen of interest;
   (b) a diluent for a serum or plasma sample;
   (c) a labeled type IV Fc receptor;
   (d) a positive control; and
   (e) a negative control.

2. The kit, according to claim 1, wherein said type VI Fc receptor is characterized by (1) having a molecular weight of about 43,000 daltons, (2) being antigenically distinct from known Fc receptors type I, II and III, and (3) displaying unique immunological profiles when compared to known type IV and type V receptors, or, a type VI Fc receptor characterized by (1) having a molecular weight of about 90,000 daltons, (2) being antigenically distinct from known Fc receptors type I, II and III, and (3) displaying unique immunological profiles when compared to known type IV and type V receptors.

* * * * *

UNITED STATES PATENT AND TRADEMARK OFFICE
CERTIFICATE OF CORRECTION

PATENT NO. : 4,948,725

DATED : August 14, 1990

INVENTOR(S) : Michael D.P. Boyle

It is certified that error appears in the above-identified patent and that said Letters Patent is hereby corrected as shown below:

| | |
|---|---|
| Column 2: | lines 52-53: "2　　Docket No. UF/S&S-1　　Serial No. 131,071" should be DELETED. |
| Column 3: | line 39: "125I-rat" should read --$^{125}$I-rat--. |
| Column 10: | line 15: "RSS212" should read --RSS-212--. |
| Column 11: | line 11: "RSS212" should read --RSS-212--. |
| Column 13: | lines 44-45: "any. sample" should read --any sample--. |
| Column 14: | line 57: "experimentation o" should read --experimentation or--. |
| Column 15: | line 14: "$125_I$, $131_I$, $3_H$, $14_C$ or $35_S$" should read --$^{125}$I, $^{131}$I, $^{3}$H, $^{14}$C or $^{35}$S--. |
| Col. 16: | |
| Claim 1: | line 5: "IV" should read --VI--. |

Signed and Sealed this

Fourth Day of May, 1993

Attest:

MICHAEL K. KIRK

*Attesting Officer*　　*Acting Commissioner of Patents and Trademarks*

UNITED STATES PATENT AND TRADEMARK OFFICE
CERTIFICATE OF CORRECTION

PATENT NO. : 4,948,725

DATED : August 14, 1990

INVENTOR(S) : Michael D. P. Boyle, Kathleen J. Reis

It is certified that error appears in the above-indentified patent and that said Letters Patent is hereby corrected as shown below:

Title Page: [75] Inventor : "Michael D.P. Boyle, Gainesville, Fla." should read --Michael D.P. Boyle, Kathleen J. Reis, both of Gainesville, Fla.--.

Signed and Sealed this

Twenty-fifth Day of April, 1995

Attest:

BRUCE LEHMAN

Attesting Officer     Commissioner of Patents and Trademarks